United States Patent [19]
Fischer et al.

[11] Patent Number: 5,944,698
[45] Date of Patent: Aug. 31, 1999

[54] ADJUSTABLE FLOW SYRINGE

[75] Inventors: Dan E. Fischer; Richard N. Rachal, both of Sandy; Bruce S. McLean, West Jordan; Dan J. Bills, Sandy; Doug Hyink, West Jordan, all of Utah

[73] Assignee: Ultradent Products, Inc., South Jordan, Utah

[21] Appl. No.: 08/949,342

[22] Filed: Oct. 14, 1997

[51] Int. Cl.⁶ ................................... A61M 5/315
[52] U.S. Cl. ........................... 604/236; 604/247
[58] Field of Search ..................... 604/218, 228, 604/236, 237, 238, 246, 247, 256; 433/89, 90

[56] References Cited

U.S. PATENT DOCUMENTS

| | | | |
|---|---|---|---|
| 3,699,961 | 10/1972 | Szpur | 604/89 |
| 4,138,040 | 2/1979 | Stock. | |
| 4,332,249 | 6/1982 | Joslin | 604/36 |
| 4,768,954 | 9/1988 | Dragan. | |
| 4,811,866 | 3/1989 | Golias. | |
| 4,820,276 | 4/1989 | Moreno. | |
| 4,859,336 | 8/1989 | Savas et al.. | |
| 5,224,937 | 7/1993 | Van Der Heiden et al. | 604/200 |
| 5,246,371 | 9/1993 | Fischer. | |
| 5,259,956 | 11/1993 | Mercer et al.. | |
| 5,387,103 | 2/1995 | Fischer. | |
| 5,643,227 | 7/1997 | Stevens | 604/247 |

*Primary Examiner*—Wynn Wood Coggins
*Assistant Examiner*—A. T. Nguyen
*Attorney, Agent, or Firm*—Workman, Nydegger, Seeley

[57] ABSTRACT

An adjustable flow syringe is provided that comprises a slidable plunger within a barrel. The barrel has a flow discharge end wherein a neck is located. The neck has a conduit extending therethrough which has an outlet and an inlet such that the conduit is in fluid communication with the barrel.

The adjustable flow syringe includes either a valve insert or a porous insert in the conduit which is configured to adjust the flow rate of a fluid leaving the syringe such that a low amount of manually applied force delivers the fluid in drops. The valve insert is formed from a resilient material and conforms to the contours of the conduit. The valve insert has a portion that extends across the conduit outlet with an opening formed therethrough. The porous insert is formed from a porous material and is configured with a shape corresponding to the shape of the conduit so that fluid passes through the conduit primarily via the pores of the porous insert.

21 Claims, 8 Drawing Sheets

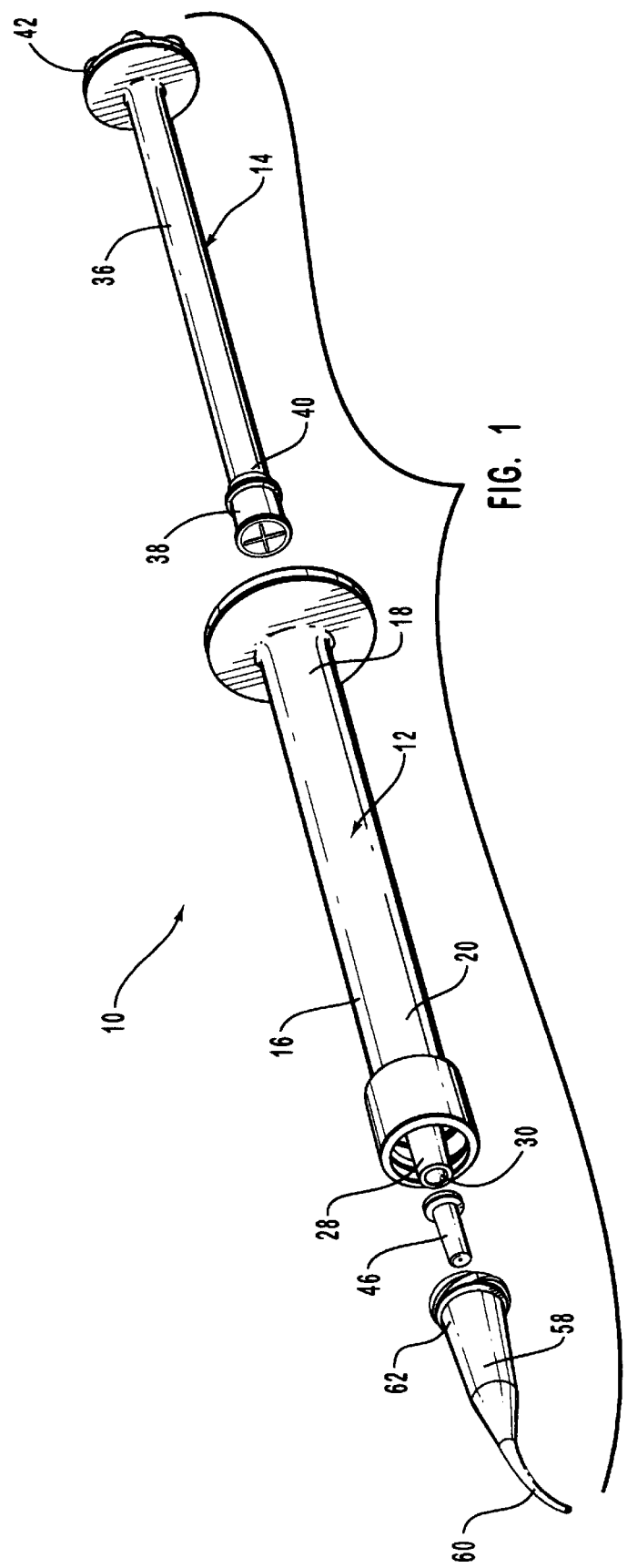

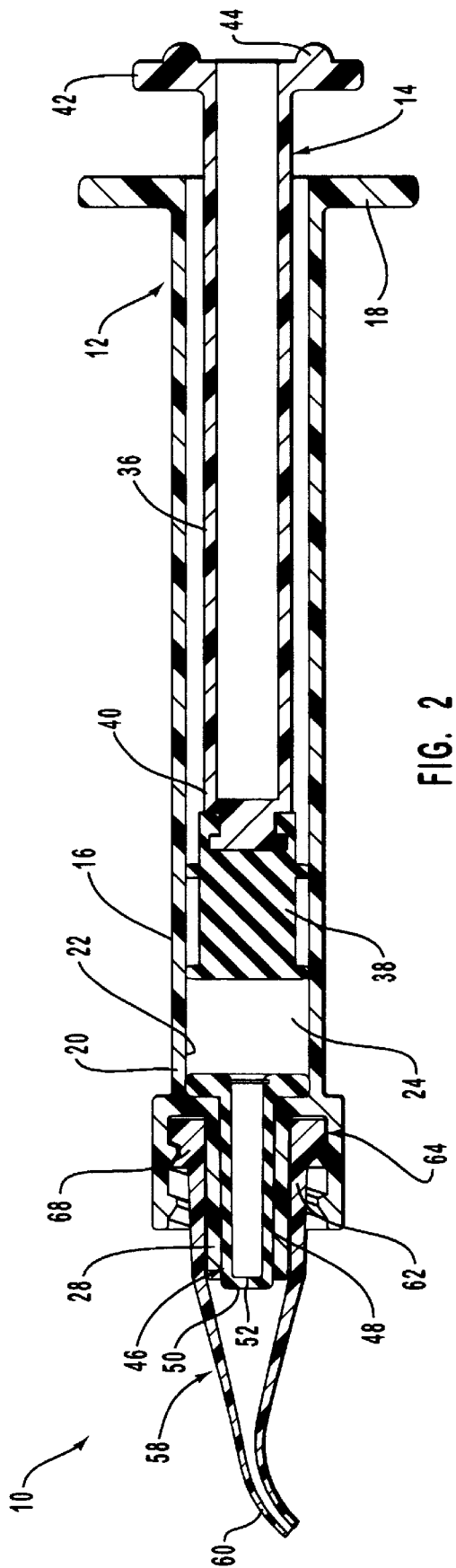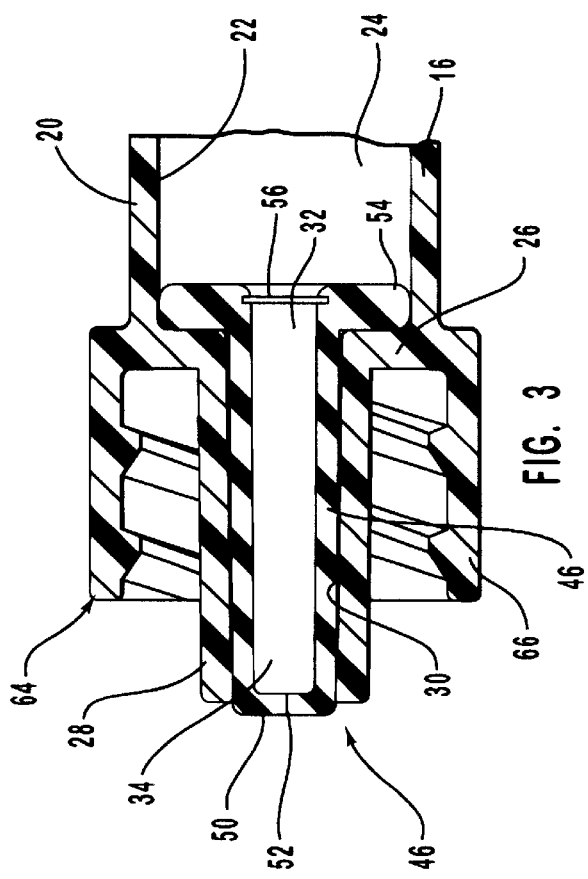

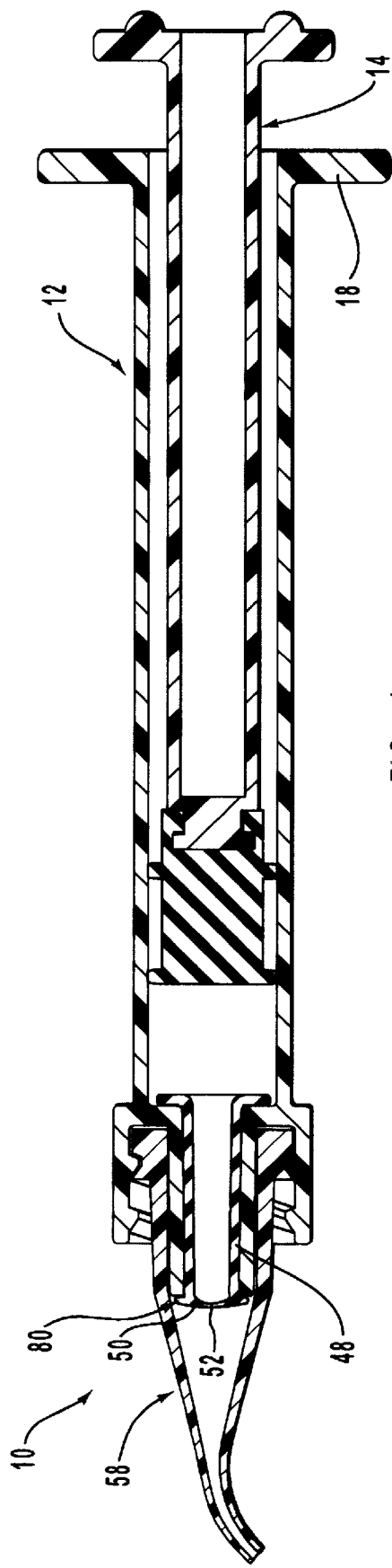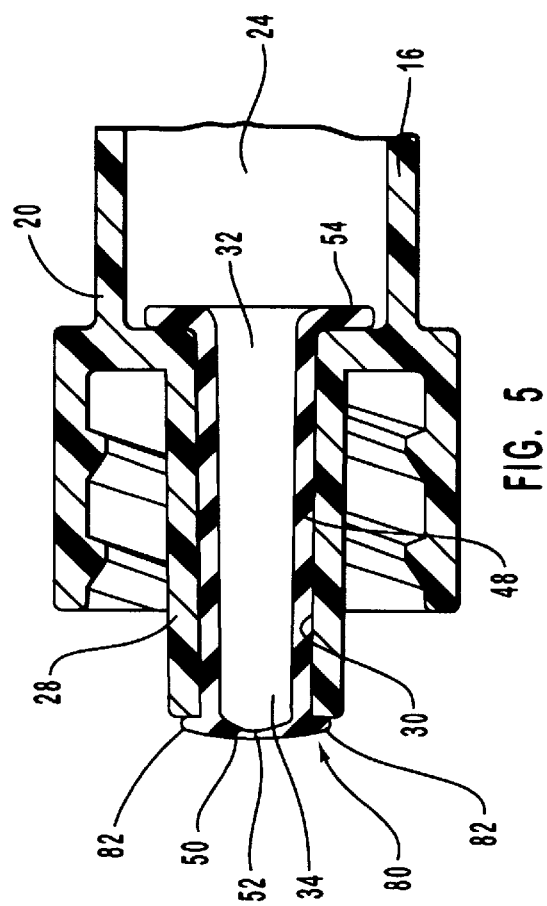

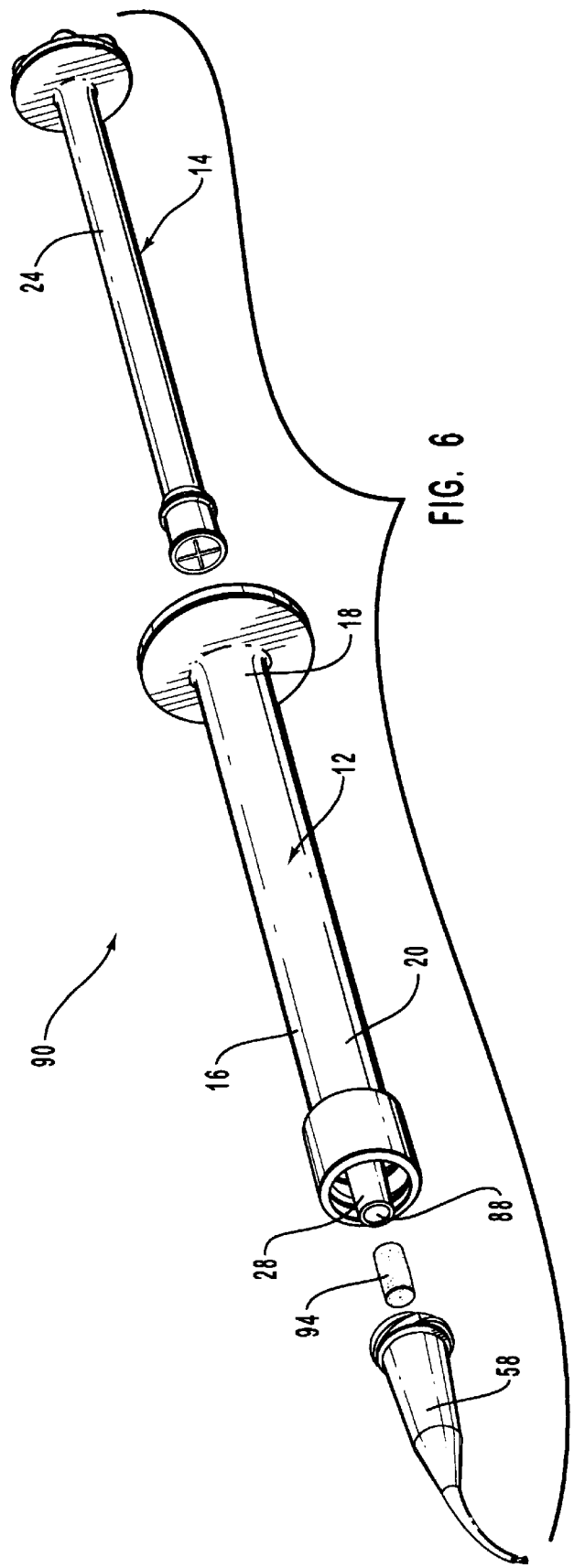

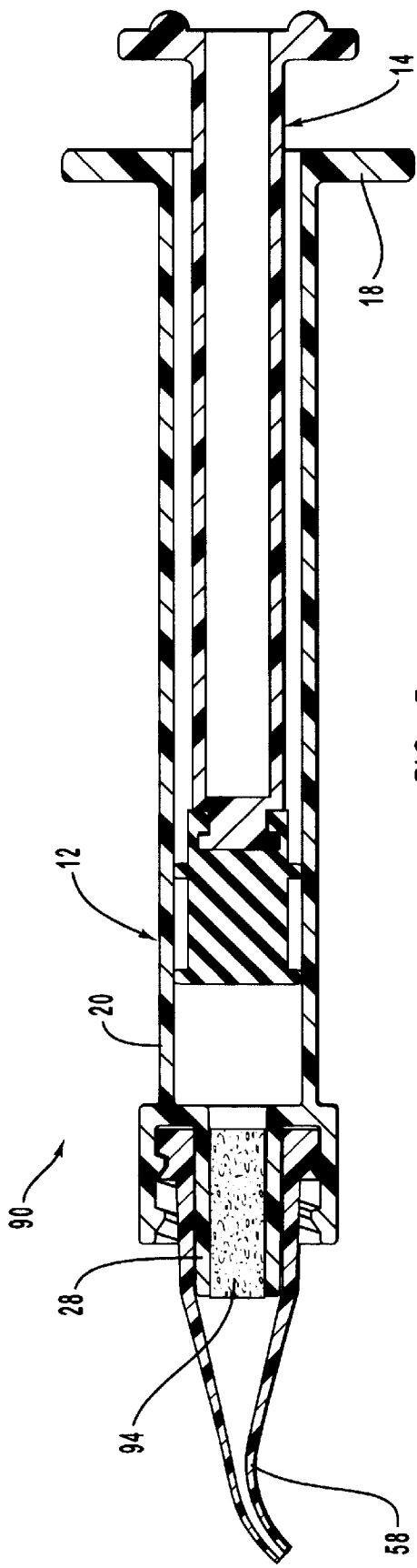
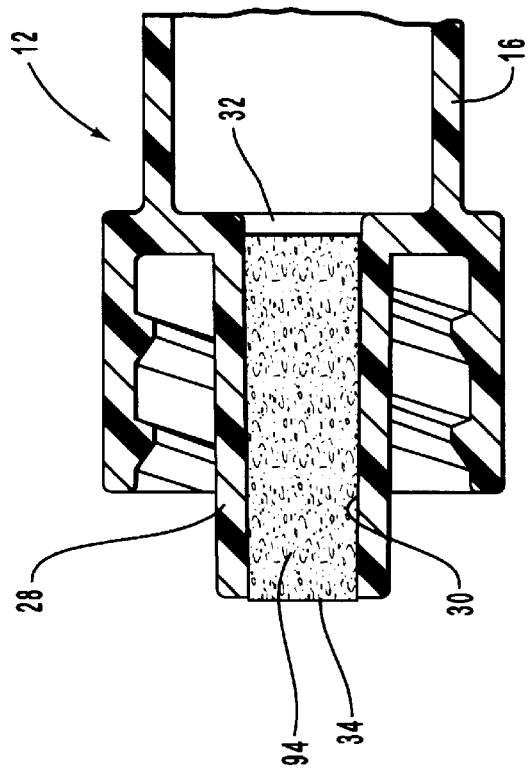
FIG. 7
FIG. 8

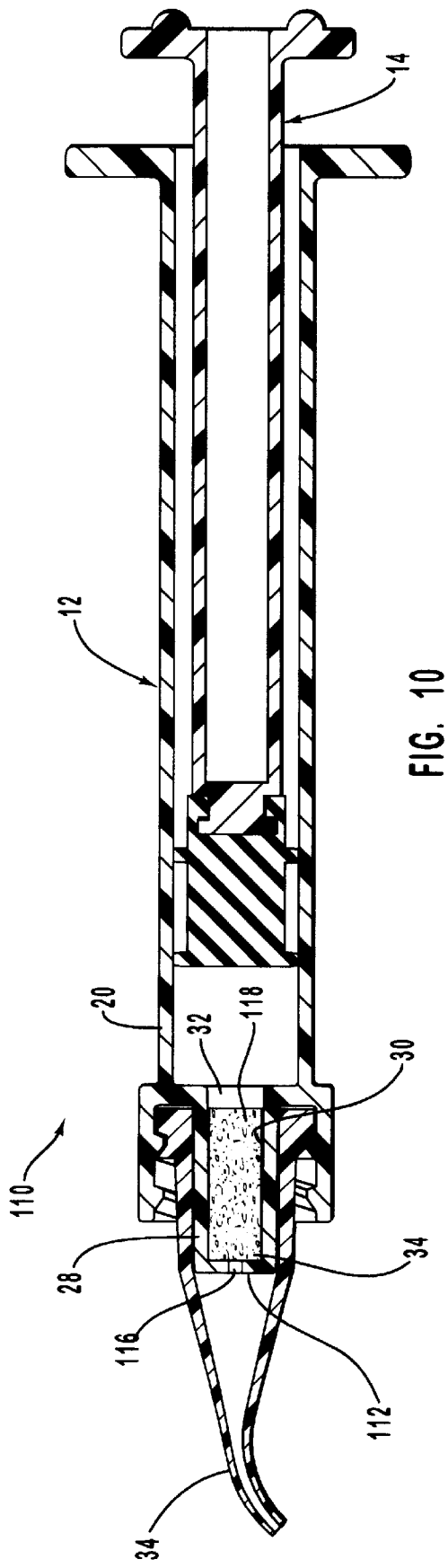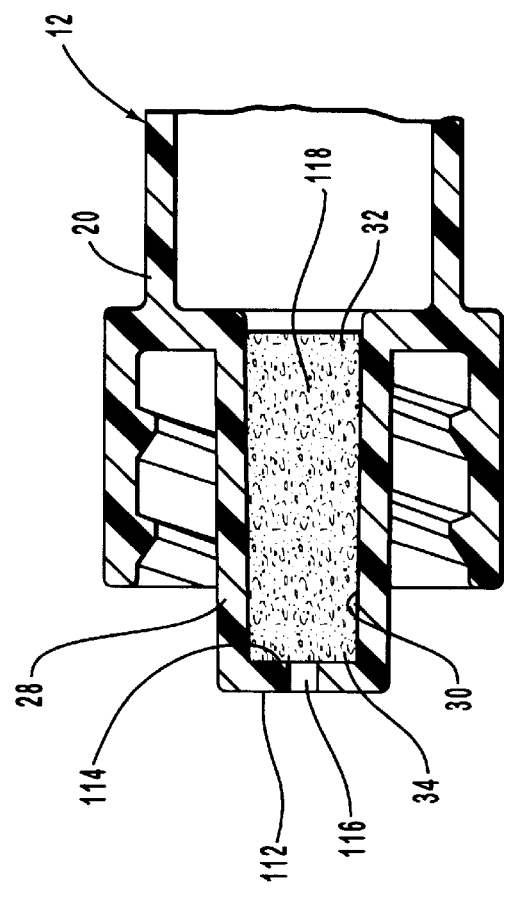
FIG. 10
FIG. 11

ADJUSTABLE FLOW SYRINGE

BACKGROUND OF THE INVENTION

1. The Field of the Invention

The present inventions related to syringes, and more particularly to variable low flow syringes for delivering fluids to a work area.

2. The Relevant Technology

Many dental, medical, and other procedures require the delivery of fluids to a specific work area in very precise quantities. Accordingly, a fluid delivery system must be able to deliver the fluid to a specific work location in precise amounts that can be closely controlled by the user. In some applications, the work area is easily and directly accessible to the user.

Various types of squeezable fluid delivery systems have been developed to deliver fluids to a precise work area. Fluid is dispensed by squeezing the container or the dispensing tip. While the squeezable fluid delivery system aids in the accurate placement of fluid, there is nothing to prevent the accidental discharge of the fluid adhesive if the user slips or the container of fluid is squeezed too hard. Accidental or excess discharge of fluid from the container is particularly problematic with low viscosity fluids such as acetone, water, or alcohol. In addition, this fluid delivery system may only be used if there is direct unimpeded access to the worksite.

The most commonly used fluid delivery system is a syringe. Fluids are delivered to a specific work area using a syringe in a variety of situations. Typical syringes include a barrel and a plunger. The barrel acts as a fluid reservoir and the plunger is disposed in the barrel. Fluid is pushed out of the fluid reservoir when the plunger is depressed. The syringe has some type of tip attached to the end of the barrel for delivering fluid to a specific work area.

During use, a syringe is typically held in one hand. The other hand is usually busy keeping the work area clean or holding something. The user of the syringe must usually hold the syringe in one hand and depress the plunger with the same hand that is holding the syringe. It is important that the plunger be depressed with a great deal of control to insure that the correct amount of fluid is forced out of the syringe. It is difficult to precisely control how far the plunger is depressed and correspondingly how much fluid is dispense. The control problem becomes even more accentuated when this type of fluid delivery system is used with fluids having a low viscosity and, consequently, requiring little force to discharge the fluid from the barrel. An accidental slip while depressing the plunger can easily empty the entire fluid reservoir of a low viscosity fluid.

Syringes are often used as a fluid delivery system in dental procedures. In dental procedures, the worksite tends to be remote and difficult to reach because of space limitations. As previously mentioned, it is often difficult to control the delivery of the fluid to the specific work area. In many dental procedures, it is important to deliver small, discrete quantities of fluid.

Another problem associated with conventional syringes, particularly prefilled syringes, is evaporation or leakage of a fluid from the barrel or fluid reservoir of the syringe. Syringes, such as those used in dental procedures, are often prefilled with the desired fluid prior to being stored and shipped to a customer. Such prefilled syringes are often utilized to deliver a certain volume of fluid so it is preferable for the volume to remain constant during shipping and storage. Evaporation is a particularly challenging problem as many of the fluids that are used with the dental syringes are volatile or are fluids that have a low viscosity. Accordingly, when a dentist is ready to use a syringe containing a fluid with a high content of a volatile fluid such as alcohol there may be significantly less fluid in the syringe compared to when it was filled. Not only is this frustrating to the customer, but the leakage and evaporation of volatile fluids may compromise certain procedures due to delivery of an inadequate amount of fluid.

One method of minimizing the problems associated with potential leakage or evaporation is to attach a tip or cap to the syringe prior to shipping or storing the product. Using tips to minimize the problems of leakage and evaporation is problematic as the tip attached to a syringe during shipping may not be the tip desired by the end user, such as a dentist, for a particular procedure as there are a variety of tips which are each optimal for different procedures. The result is a decrease in efficiency for the user of the syringe as it is then necessary to take the time to change the tips. To avoid the need to change tips, manufacturers can make syringes available containing identical fluids with different tips. This increases the inventory costs of the manufacturer which increases the price of the syringe.

Caps are generally more effective than tips in reducing evaporation, however, there are also problems associated with the use of caps. Caps decrease the efficiency of procedures involving such syringes and increase the costs of such syringes as the cap must be replaced by a tip for use in delivering the fluid.

In addition, neither tips or caps completely solve the problems of evaporation or leakage of fluids from syringes. Accordingly, it would be advantageous to have a fluid delivery system, such as a syringe, that can be prefilled with a desired fluid and then stored and shipped with substantially no leakage or evaporation of the fluid. It would also be advantageous to be able to store and ship prefilled syringes without a tip or a cap.

In conclusion, it would be advantageous to have a fluid delivery system that will deliver only drops of fluid. There are certain situations where initially only drops of fluid are needed and later a steady or increased flow of fluid is required. It would be advantageous to have a fluid delivery system that is configured to provide sufficient control to deliver fluid a drop at a time as well as being able to gradually increase the flow rate to a stream of fluid.

BRIEF SUMMARY AND OBJECTS OF THE INVENTION

It is an object of the present invention to provide a syringe that delivers fluid a drop at a time in response to a little amount of force within a range of forces that can be manually applied to the plunger of the syringe.

It is another object of the present invention to provide a syringe that is capable of adjusting the flow rate of fluid from the syringe such that a low level of force within a range of forces that can be manually applied to advance the plunger delivers a fluid a drop at a time and a high level of force delivers fluid in a stream.

Another object of the present invention is to provide a syringe capable of delivering fluid only a drop at a time regardless of the amount of force used to depress the plunger.

Another object of the present invention is to provide a syringe that is capable of withstanding accidental slips and depressions of the plunger without discharging excess fluid.

Yet another object of the present invention is to provide a syringe that is capable of delivering even low viscosity fluids a drop at a time regardless of how hard the plunger of the syringe is depressed.

It is a further object of the present invention to provide a syringe that can deliver a drop of fluid to a precise location.

Finally, it is an object of the present invention to provide a syringe that can be prefilled with a desired fluid and then stored and shipped with substantially no leakage or evaporation of the fluid without a tip or a cap.

These and other objects and features of the present invention will become more fully apparent from the following description and appended claims, or may be learned by the practice of the invention as set forth hereinafter.

To achieve the foregoing objects, in accordance with the invention as embodied and broadly described herein, an adjustable flow syringe is provided that comprises a unique flow regulator that is configured to prevent accidental discharge of a fluid and allows extremely precise and controlled dispensing of even a low viscously fluid. The flow regulator also preferably minimizes any potential leakage or evaporation of fluid during shipping and storing of syringes that have been prefilled with a fluid.

The syringe comprises a barrel and a slidable plunger. The barrel has a flow discharge end and a plunger receiving end with an opening formed therein. The flow discharge end of the barrel has a neck with a conduit extending through the neck that is in fluid communication with the barrel. The conduit has an inlet and an outlet. The plunger is disposed in the barrel and slides through the opening in the plunger receiving end of the barrel toward the flow discharge end of the barrel.

In one embodiment, the flow regulator of the adjustable flow syringe comprises a valve insert that is disposed in the conduit which selectively controls fluid flow in response to pressure created by the forces applied to the plunger. The valve insert includes a body portion disposed within the conduct and a resilient, silicon rubber membrane portion substantially across the outlet of the conduit at the flow discharge end of the barrel. The membrane having an opening formed therethrough that is configured to distort in response to the pressure resulting from an increase in the force used to manually advance the plunger within the barrel.

In another embodiment, the flow regulator of the adjustable flow syringe comprises a porous insert which restricts the flow rate of a fluid in the syringe such that any force within a range of forces that can be manually applied to the plunger delivers fluid at a substantially constant flow rate. The porous insert is disposed in the conduit at the flow discharge end of the barrel. The porous insert is configured to restrict the flow rate of fluid so as to make the syringe capable of dispensing the fluid only as drops of fluid as the plunger is manually advanced within the barrel.

Both the valve insert and the porous insert are configured for adjusting the flow rate of a fluid leaving the syringe such that a low amount of force within the range of forces that can be manually applied to the plunger delivers the fluid a drop at a time.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which:

FIG. 1 is an exploded perspective view of one embodiment of the syringe;

FIG. 2 is a cross-sectional elevation view of the structure of FIG. 1;

FIG. 3 is an enlarged partial cross-sectional view of the structure of FIG. 2;

FIG. 4 is a cross-sectional elevation view of another embodiment of the syringe;

FIG. 5 is an enlarged partial cross-sectional view of the structure of FIG. 4;

FIG. 6 is an exploded perspective view of another embodiment of the syringe;

FIG. 7 is a cross-sectional elevation view of the structure of FIG. 6;

FIG. 8 is an enlarged partial cross-sectional view of the structure of FIG. 7;

FIG. 10 is a cross-sectional view of the structure of FIG. 9; and

FIG. 11 is an enlarged partial cross-sectional view of the structure of FIG. 10.

DETAILED DESCRIPTION OF THE PREFERRED EMBODIMENTS

Figure 3B:
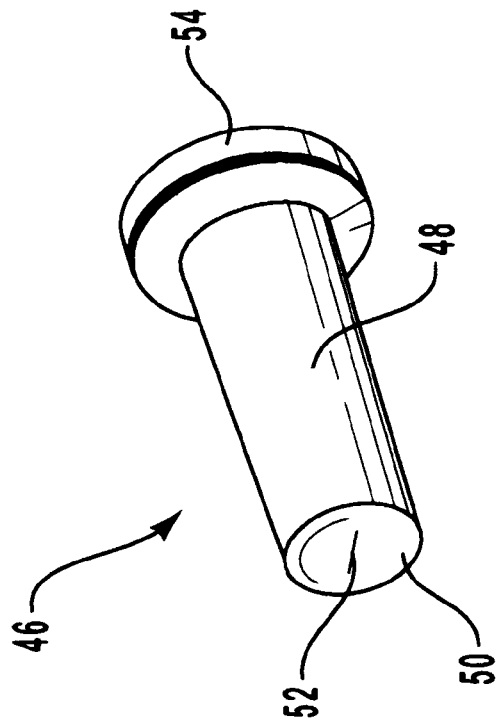
FIG. 3B is an enlarged perspective view of an alternate embodiment of the valve insert from FIG. 1.

The present invention relates to a fluid delivery system, such as a syringe, with a unique flow regulator that is configured to prevent accidental discharge of a fluid, allows extremely precise and controlled dispensing of even a low viscosity fluid and preferably minimizes any potential leakage or evaporation of fluids in prefilled syringes during shipping and/or storing. The syringe has a barrel which acts as a fluid reservoir and a slidable plunger which is used to dispense the fluid from the fluid reservoir. In each embodiment illustrated in FIGS. 1–11, the slidable plunger and the barrel are configured to cooperate together to force fluid through the unique flow regulator and these optionally deliver fluid through a hollow tip.

As shown in FIGS. 1–3 at 10, the adjustable flow syringe comprises a barrel 12 configured to receive a plunger 14. Barrel 12 comprises an elongated tubular body 16 with a plunger receiving end 18 and flow discharge end 20. Tubular body 16 has an interior surface 22 which defines a fluid reservoir 24 within barrel 12 as depicted in FIGS. 2 and 3. At plunger receiving end 18 of tubular body 16, interior surface 22 defines an opening that is sufficiently large to receive plunger 14 as illustrated in FIGS. 2 and 3. In the figures, barrel 12 and plunger 14 are depicted as being substantially cylindrical-shaped. Barrel 12 and plunger 14 must be similarly sized and configured so as to cooperate together. Barrel 12 and plunger 14 may, however, have other shapes including having a elliptical or square cross-section that is perpendicular to the longitudinal axis of barrel 12.

At flow discharge end 20 of barrel 12, an annular shoulder 26 extends from interior surface 22 of tubular body 16 inward within fluid reservoir 24 as illustrated in FIG. 3. An elongated and hollow neck 28 extends substantially perpendicularly from annular shoulder 26. Neck 28 is depicted in FIG. 1 as being substantially cylindrical-shaped. Neck 28 may, however, have other configurations such as being an elongated elliptical member and perform the function thereof equally effectively. The inside diameter of neck 28 defines a conduit 30. Referring to FIG. 3, conduit 30 has an inlet 32 and an outlet 34 and is in fluid communication with fluid reservoir 24 in barrel 12. The result of this configuration is that the diameter of conduit 30 formed by neck 28 is smaller than the diameter formed by interior surface 22 of tubular body 16. Barrel 12 that comprises hollow tubular body 16 is one example of structure capable of performing the function of a reservoir means for containing a fluid until pressure is applied to the fluid.

As illustrated in FIGS. 1 and 2, plunger 14 comprises an elongated shaft 36 and resilient plug 38. Plunger 14 has a forward end 40 and a thumb pressing end 42. Resilient plug 38 is attached to forward end 40 of elongated shaft 36. Plunger 14 is displaceable by sliding within tubular body 16 of barrel 12. When plunger 14 is disposed within tubular body 16 of barrel 12, resilient plug 38 seals the fluid within fluid reservoir 24.

One embodiment of plunger 14, as illustrated in FIG. 2, is hollow. Thumb pressing end 42 of plunger 14 has an optional raised textured pattern 44 formed on the surface of thumb pressing end 42 that is contacted by the thumb of a user. Raised textured pattern 44 prevents the thumb of the user from slipping off of thumb pressing end 42 when plunger 14 is depressed to advance plunger 14 in barrel 12. Plunger 14 is one example of a structure capable of performing the function of a dispensing means for controlled discharge of the fluid from fluid reservoir 24 in body 16 by applying pressure to the fluid within fluid reservoir 24 to dispense the fluid. Various other embodiments of a dispensing means are equally effective in carrying out the intended function thereof.

Figure 3A:
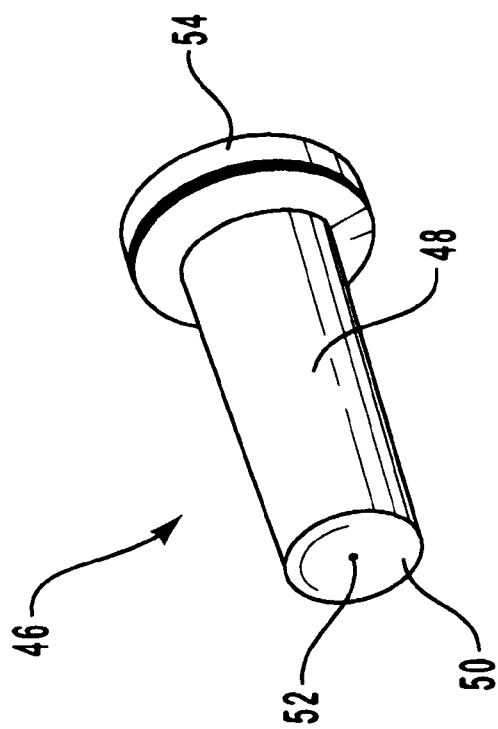
FIG. 3A is an enlarged perspective view of the valve insert from FIG. 1.

Referring to FIGS. 2–3A adjustable flow syringe 10 further comprises valve insert 46. Valve insert 46 is one example of structure capable of performing the function of a valve means for selectively controlling fluid flow in response to pressure created by forces applied to plunger 14 such that when a low amount of force is manually applied fluid is delivered a drop at time and when a high amount of force is manually applied fluid is delivered substantially in a stream. Various other embodiments of structure capable of performing the function of such a valve means are equally effective in carrying out the intended function thereof.

Valve insert 46 is configured to selectively control the fluid flow from fluid reservoir 24 in response to pressure created by forces applied to thumb pressing end 42 of plunger 14 by the user of syringe 10. Valve insert 46 is located at flow discharge end 20 of barrel 12 and is disposed primarily within conduit 30 formed by neck 28. As depicted in FIGS. 3 and 3A, valve insert 46 primarily comprises an elongated body portion 48 and a resilient membrane 50 having an opening 52 formed therein.

Body portion 48 is configured to closely correspond or conform to the dimensions and any contours of conduit 30 formed by neck 28 such that body portion 48 of valve insert 46 contacts conduit 30 along the entire length thereof. Resilient membrane 50 is disposed in outlet 34 of conduit 30 and extends substantially across outlet 34 of conduit 30. Resilient membrane 50 is configured to selectively control the flow rate of fluid from fluid reservoir 24 in response to pressure created by forces applied to plunger 14. Resilient membrane 50 has a preferred thickness in metric units of about 0.2 mm to about 1.5 mm. When measured in English units, resilient membrane 50 has a preferred thickness of about 0.01 inches to 0.05 inches.

Opening 52 and resilient membrane 50 are configured so that opening 52, in particular, distorts in response to the pressure resulting from the force used to manually advance plunger 14 within barrel 12. Opening 52 in resilient membrane 50 is preferably configured such that the resiliency of resilient membrane 50 can be utilized to enable opening 52 to remain essentially closed until pressure is applied by the fluid being pushed down by the action of pushing plunger 14. Accordingly, a syringe with a valve insert comprising a resilient membrane with such an opening therein enables the syringe to be prefilled with a fluid, then be shipped and/or stored, and be ready for use with substantially no leakage or evaporation of the fluid compared to the amount of fluid originally added.

In one embodiment depicted in FIGS. 1 and 3A, opening 52 is a pin hole. FIG. 3B illustrates a valve insert 46 with an opening 52 that is shaped as an elongated slit. It can be appreciated that either shape of opening 52 performs the function thereof equally effectively. It is contemplated that opening 52 may have other configurations such as a curved slit or curvilinear slit. In addition to pinholes and slits, opening 52 may have any suitable configuration such that the opening has a cross-sectional shape that is oval, triangular, etc.

Upon low levels of force being applied to plunger 14, opening 52 allows fluid to pass therethrough at a reduced rate of flow such that fluid is dispensed a drop at a time. As the pressure increases, opening 52 in resilient membrane 50 opens and allows increased flow of fluid through opening 52.

As shown in FIG. 3, valve insert 46 also comprises an annular ring 54 that extends substantially perpendicularly and radially outward from elongated body portion 48. When body portion 48 is disposed in conduit 30, annular ring 54 contacts annular shoulder 26. Annular shoulder 26 and annular ring 54 keep elongated body portion 48 and resilient membrane 50 in place in outlet 34 of conduit 30. Annular shoulder 26 and annular ring 54 are one embodiment of structure capable of performing the function of a retention means for keeping body portion 48 of valve insert 46 in place relative to conduit 30. The retention means also further enhance the ability of syringes utilizing a structure such as valve insert 46 to be prefilled with a fluid, then be shipped and/or stored, and be ready for use with substantially no leakage or evaporation of the fluid compared to the amount of fluid originally added.

The retention means also comprises compressive forces acting on body portion 48. Body portion 48 preferably has a slightly larger cross-section than the cross section of conduit 30. As a result, upon being disposed in conduit 30 within neck 28, compressive forces acting substantially radially inward on body portion 48 help keep valve insert 46 in place in conduit 30.

In one embodiment illustrated in FIGS. 1–3, the interior surface of body portion 48 of valve insert 46 has an optional groove 56 formed therein that is used to assist in positioning valve insert 46 in conduit 30 by an interference fit. Grove 56 is configured to cooperate with the tools used in the assembly process. Groove 56 may have various other configurations.

One embodiment of an adjustable flow syringe 10 illustrated in FIG. 1 comprises an optional hollow tip 58. Hollow tip 58 has a fluid dispensing end 60 and a proximal end 62. Proximal end 62 of hollow tip 58 is capable of being connected to flow discharge end 20 of barrel 12. FIGS. 1 and 2 illustrate one possible embodiment of hollow tip 58. It is intended that adjustable flow syringe 10 can be used with other configurations of hollow tip 58 depending on the specific application and needs of the user. Various embodiments of hollow tip 58 are equally effective in carrying out the intended function thereof. By way of example and not limitation, fluid dispensing end 60 of hollow tip 58 could have a different curvature than that illustrated in FIGS. 1 and 2.

Hollow tip 58 is configured to be releasably connected to flow discharge end 20 of barrel 12. Flow discharge end 20 of barrel 12 has a male Luer connector 64 formed thereon. Male Luer connector 64 includes neck 28 and a threaded collar 66. Proximal end 62 of hollow tip 58 has as a cooperating female Luer connector 68 formed thereon configured to releasably cooperate with male Luer connector 64 on flow discharge end 20 of barrel 12. The configuration and outside diameter of neck 28 of male Luer connector 64 preferably correspond to American National Standards Institute (ANSI) standards.

Male and female Luer connectors 64 and 68, respectively, are one example of structure capable of performing the function of a coupling means for attaching hollow tip 58 to barrel 12. Various other embodiments of a coupling means equally effective in carrying out the intended function thereof. By way of example and not limitation, hollow tip 58 may be fixedly attached to flow discharge end 20 of barrel 12 using an adhesive, snap fit or other conventional connectors. Where it is desired that hollow tip 58 be releasably attached to flow discharge end 20 of barrel 12, hollow tip 58 and flow discharge end 20 of barrel 12 may have other releasable fasteners, such as complimentary sets of barbs or ridges.

FIGS. 4 and 5 depict another embodiment of the valve means. The majority of features previously discussed apply to valve insert 80. Therefore, features that are not affected are identified with the same reference numbers as used in FIGS. 1–3. Only those features that have changed will be described in detail.

Valve insert 80 is substantially the same as valve insert 46 depicted in FIGS. 1–3. Valve insert 80 comprises body portion 48, resilient membrane 50 with opening 52 formed therein, and annular ring 54. Resilient membrane 50 of valve insert 80 has a lip 82 formed around the perimeter thereof. Lip 82 extends radially outward beyond outlet 34 of conduit 30. Lip 82 contacts a remote end of neck 28 and provides additional support to valve insert 80. Lip 82 particularly supports body portion 48 and resilient membrane 50. Lip 82 is also an example of structure capable of performing the function of a retaining means for keeping valve insert 80 in place relative to conduit 30 formed by neck 28.

In use, valve inserts 46 and 80 allow the user to depress plunger 14 and advance plunger 14 within barrel 12 using a slow but gradually increasing amount of force. Resilient membrane 50 and opening 52 within resilient membrane 50 gradually distorts. Initially when a low amount of force is used to advance plunger 14 within barrel 12 fluid is delivered a drop at a time. As the pressure is increased, opening 52 opens to allow an increased flow of fluid. The fluid flow rate increases steadily until a stream of fluid is being delivered. Resilient membrane 50 is configured such that opening 52 distorts and responds to pressure resulting from an increase in the force used to manually advance plunger 14 within barrel 12 causing opening 52 to open and to allow fluid flow through opening 52 at a rate that is substantially directly proportional to the amount of force used to advance plunger 14.

Resilient membrane 50 and opening 52 provide a great deal of precise control at low pressures with low amounts of force as well as at high pressure where high amounts of force are exerted. A low amount of force when measured in metric units is considered to be in the general range of about 5 N to about 25 N. In contrast, a high amount of force in metric units is considered to be in range from about 130 N to about 180 N. Similarly, in English units a low amount of force is considered to be in the general range of about 2 lb. to 5 lb. A high amount of force in English units is considered to be in the range of about 30 lb. to 40 lb. The maximum manually applied forces are generally not significantly greater than the above high force range.

FIGS. 6–8 depict another embodiment of the adjustable flow syringe. The majority of features previously discussed apply to adjustable flow syringe 90. As a result, features that are not affected are identified with the same reference numbers as used in FIGS. 1–3 and only those features that have changed will be described in detail.

Adjustable flow syringe 90 comprises a porous insert 94. Porous insert 94 is one example of structure capable of performing the function of a flow restrictor means for restricting the flow rate of a fluid in syringe 90 such that any force within a range of forces that can be manually applied to plunger 14 delivers fluid at a substantially constant flow rate. The embodiment of porous insert 94 depicted in FIG. 6 is substantially cylindrical in shape. It can be appreciated that porous insert 94 may have various other configurations. All that is required is that porous insert 94 be sized and configured to cooperate with the configuration of conduit 30 formed by neck 28.

As shown in FIGS. 7 and 8, porous insert 94 is disposed in conduit 30 formed by neck 28. Porous insert 94 is slightly larger than the diameter of conduit 30. In addition, neck 28 and, consequently conduit 30, are slightly tapered to conform with the ANSI standards as is commonly done in the industry. Porous insert 94 is disposed within conduit 30 by an interference fit. The interference fit of porous insert 94 within conduit 30 and the slight taper of conduit 30 causes porous insert 94 to experience radial compression forces.

The radial compression forces caused by the interference fit of oversized porous insert 94 in comparison to conduit 30 is one example of structure capable of performing the function of a retention means for keeping a porous insert 94 in place within conduit 30. Various other embodiments of structure are capable of performing the function of such a retention means equally effectively. By way of example and not limitation, rather than utilizing compression forces acting on porous insert 94 to keep porous insert 94 from being drawn back into barrel 12 when plunger 14 is moved away from flow discharge end 20 of barrel 12, an annular ridge that extends radially into conduit 30 could be formed at inlet 32 of conduit 30.

Figure 9:
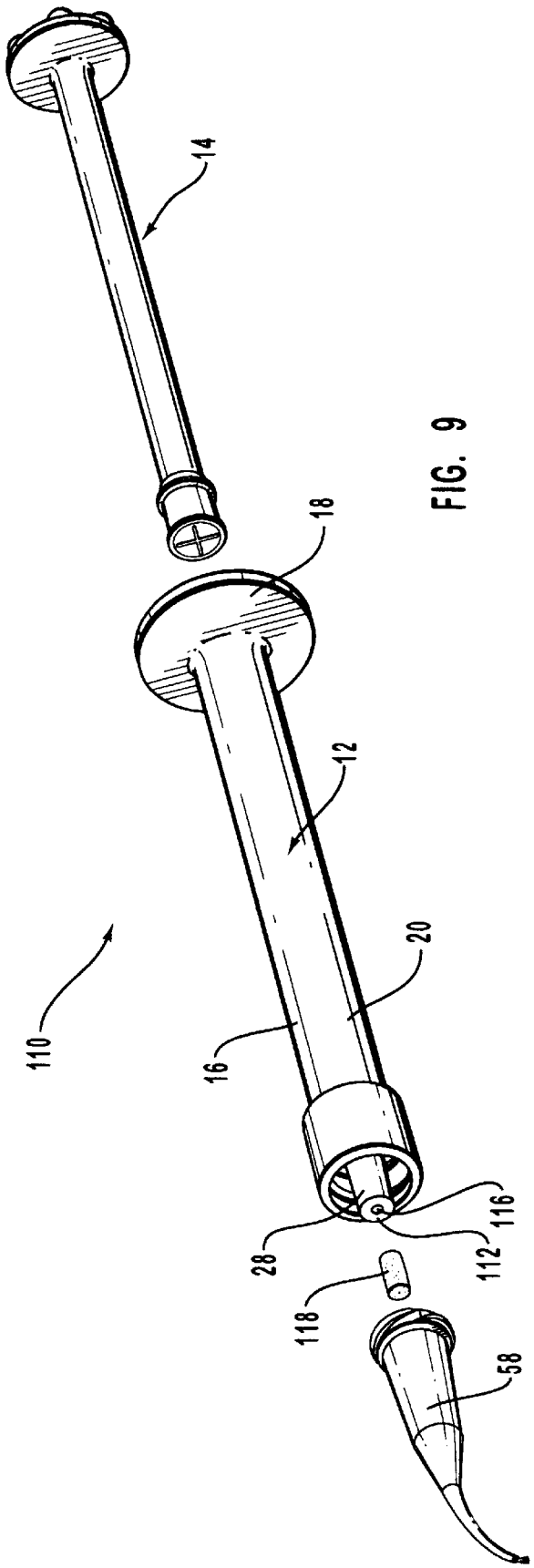
FIG. 9 is an exploded perspective view of another embodiment of the syringe.

FIGS. 9–11 depict another embodiment of the adjustable flow syringe at 110. Neck 28 of syringe 110 has an end wall 112 extending radially and substantially perpendicularly inward. End wall 112 has an inside surface 114. End wall 112 has an aperture 116 formed therein. End wall 112 substantially closes outlet 34 of conduit 30 at flow discharge end 20 of barrel 12. Aperture 116 preferably has a diameter in metric units in the range of about 0.1 mm to about 2 mm. It is preferred that aperture 116 has a diameter range of about 0.2 mm to about 1.3 mm. When measured in English units, aperture 116 preferably has a diameter range of about 0.005 inches to about 0.08 inches. Preferably, aperture 116 has a diameter of about 0.01 inches to 0.05 inches.

As shown in FIG. 11, one end of porous insert 118 contacts inside surface 114 of end wall 112. Aperture 116 and porous insert 118 are capable of restricting the flow rate of a fluid from the barrel such that any force within a range of forces that can be applied manually to plunger 14 delivers fluid at a substantially constant flow rate. In this embodiment, porous insert 118 in combination with aperture 116 formed in end wall 112 are one example of structure capable of performing the function of a flow restrictor means for restricting the flow rate of a fluid in the syringe such that any force within a range of forces that can be manually applied to plunger 14 to advance plunger 14 in barrel 12 delivers fluid at a substantially constant flow rate. Various other embodiments of structure are capable of performing the function of such a flow restrictor means equally effectively.

Porous inserts 94 and 118 comprises material selected from the group consisting of cotton, felt, polyethylene, polytetrafluoroethylene, polypropylene, and polyvinylidene fluoride. Preferably, porous inserts 94 and 118 comprise material selected from the group consisting of polyethylene, polytetrafluoroethylene, polypropylene and polyvinylidene fluoride. Most preferably, porous inserts 94 and 118 comprise polypropylene. Porous inserts 94 and 118 may have a pore size of about 5 microns to about 250 microns. In one preferred embodiment, porous insert 94 has a pore size of about 5 microns to about 50 microns.

Porous inserts 94 and 118 adjust the flow rate of fluid leaving syringes 90 and 110, respectively, such that a low amount of force applied to plunger 14 delivers fluid a drop at a time. In fact, porous inserts 94 and 118 restrict the flow rate of fluid in syringe 90 such that any force within the range of forces that can be manually applied to plunger 14 delivers fluid at a substantially constant flow rate. Aperture 116 in combination with porous insert 118 is configured to restrict the flow rate of a fluid so as to make syringe 90 capable of dispensing fluid only as drops of fluid when plunger 14 is manually advanced within barrel 12.

The configurations of porous inserts 94 and 118 enable syringes to be prefilled with a fluid, then be shipped and/or stored, and be ready for use with substantially no leakage or evaporation of the fluid compared to the amount of fluid originally added. The ability of syringes utilizing porous inserts 94 and 118 to minimize leakage and/or evaporation is further enhanced by the use of retention means for keeping a porous insert within conduit 30.

The structures disclosed herein that perform the function of the valve means and the flow restrictor means are examples of a flow regulator means for adjusting the flow rate of the fluid leaving syringe 10 such that a low amount of force within the range of forces that can be manually applied to plunger 14 delivers fluid a drop at a time. Examples of flow regulator means including valve insert 46, porous insert 94 and porous insert 118 are each configured to adjust the flow rate of fluid such that the adjustable syringe dispenses even low viscosity fluids such as acetone, alcohol, and water as drops of fluid when a low amount of pressure is manually applied. Additionally, the embodiments of structure performing the function of a flow regulator means have the advantage that when no force is exerted upon plunger 14 there is substantially no flow out of fluid out of the syringe. In addition to substantially preventing or at least minimizing leakage of fluids that have been prefilled in fluid reservoir 24, the flow regulator means also substantially prevents or at least minimizes evaporation of fluids from the syringe including low viscosity or volatile fluids.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An adjustable flow syringe comprising:
    a hollow body having a flow discharge end and a plunger receiving end with an opening formed therein, said hollow body defining a fluid reservoir configured to contain said fluid;
    a plunger slidably disposed in said hollow body said plunger applying pressure to said fluid within said fluid reservoir to dispense said fluid through said opening in said plunger receiving end of said hollow body; and
    a valve insert disposed at said flow discharge end, said valve insert comprising a resilient membrane having an opening formed therethrough, said resilient membrane and said opening being configured to distort so as to adjust the flow rate of said fluid leaving the syringe in response to the force applied to the plunger, so as permit delivery of said fluid a drop at a time when needed.

2. An adjustable flow syringe comprising:
    a barrel comprising a hollow body having a flow discharge end and a plunger receiving end with an opening formed therein, said hollow body defining, a fluid reservoir configured to contain fluid;
    a plunger slidably disposed in said hollow body; and
    valve means, disposed at said flow discharge end, for selectively controlling fluid flow in response to pressure created by force applied to said plunger when expelling fluid from the discharge end, said valve means comprising resilient opening means for distorting in response to the force applied to the plunger, thereby adjusting the flow rate of the fluid leaving the syringe to permit delivery of the fluid a drop at a time when needed.

3. An adjustable flow syringe as recited in claim 2, wherein said resilient opening means comprises a resilient membrane that is substantially composed of material selected from the group consisting of elastomeric polymers and silicon rubber.

4. An adjustable flow syringe as recited in claim 3, wherein said resilient membrane maintains the opening in essentially a closed position until pressure is applied by fluid being pushed down as the plunger is advanced within the barrel, whereby the barrel can be prefilled with a fluid without substantial leakage or evaporation of the fluid during subsequent storage.

5. An adjustable flow syringe as recited in claim 4, wherein said opening is substantially round.

6. A variable flow syringe comprising:
    a barrel comprising a hollow body having a flow discharge end and a plunger receiving end with an opening formed therein, said hollow body defining a fluid reservoir configured to contain fluid, said barrel having a neck at said fluid discharge end with a conduit extending through said neck that is in communication with said fluid reservoir, said conduit having an inlet and an outlet;

a plunger slidably disposed in said fluid reservoir through said opening in said plunger receiving end of said barrel; and a valve insert disposed at said flow discharge end, said valve insert comprising a resilient membrane having an opening formed therethrough, said resilient membrane and said opening being configured to distort so as to adjust the flow rate of said fluid leaving the syringe in response to the force applied to the plunger, so as permit delivery of said fluid a drop at a time when needed.

7. A variable flow syringe as recited in claim 6, wherein said valve insert is at least partially disposed in said conduit of said neck.

8. A variable flow syringe as recited in claim 7, wherein said valve insert comprises:

a body portion disposed primarily in said conduit at said flow discharge end of said barrel; and said resilient membrane is attached to one end of said body portion proximate to said outlet of said conduit.

9. A variable flow syringe as recited in claim 8, wherein said opening is configured such the resilient membrane maintains the opening in essentially a closed position until pressure is applied by fluid being pushed down as the plunger is advanced within the barrel, whereby the barrel can be prefilled with a fluid without substantial leakage or evaporation of the fluid during subsequent storage.

10. A variable flow syringe as recited in claim 8, wherein said opening is substantially round.

11. A variable flow syringe as recited in claim 8, wherein said resilient membrane is disposed substantially across said outlet of said conduit.

12. A variable flow syringe as recited in claim 11, wherein said resilient membrane is substantially composed of an elastomeric rubber material.

13. A variable flow syringe as recited in claim 8, further comprising a retention means for keeping said body portion in place relative to said conduit.

14. A variable flow syringe as recited in claim 13, wherein said retention means comprises:

(a) an annular shoulder extending between said hollow body of said barrel and said conduit of said neck, said annular shoulder being proximate to said inlet of said conduit of said neck at said fluid discharge end of said barrel; and (b) an annular ring attached to the opposite end of said body portion from said resilient membrane, said annular ring extending radially outward from said body portion, said annular ring being configured to contact said annular shoulder.

15. A variable flow syringe as recited in claim 14, wherein said retention means further comprises a lip extending radially outward from said resilient membrane, said lip being configured to engage said neck proximate to said outlet of said conduit.

16. A variable flow syringe comprising:

(a) a barrel comprising a hollow body having a flow discharge end and a plunger receiving end with an opening form therein, said hollow body defining a fluid reservoir configured to contain fluid, said barrel having, a substantially cylindrical-shaped neck at said flow discharge end with a conduit extending through said neck, said conduit having an inlet and an outlet, said conduit having an inner diameter smaller than the inner diameter of said barrel;

(b) a plunger disposed in said fluid reservoir, said plunger being slidable through said opening in said plunger receiving end of said barrel towards said flow discharge end thereof;

(c) an annular shoulder extending between said hollow body of said barrel and said conduit of said neck, said annular shoulder being proximate to said inlet of said conduit of said neck at said flow discharge end of said barrel; and (d) a valve comprising:

(i) a body portion disposed primarily in said conduit of said neck at said flow discharge end of said barrel, said body portion having one end proximate to said outlet of said conduit and another end proximate to said inlet of said conduit;

(ii) a resilient membrane attached to the end of said body portion proximate to said outlet of said conduit, said resilient membrane being disposed substantially across said outlet of said conduit, said resilient membrane having an opening formed therein, said resilient membrane being configured such that said opening in said resilient membrane distorts and responds to the pressure resulting from an increase in the force used to manually advance said plunger within said barrel causing said opening to open and to allow fluid flow through said opening at a rate that is substantially directly proportional to the amount of said force used to advance said plunger; and (iii) an annular ring attached to the end of said body portion proximate to said inlet of said conduit, said annular ring being configured to contact said annular shoulder and to keep said body portion in place relative to said conduit.

17. A variable flow syringe as recited in claim 16, wherein said resilient membrane is substantially composed of an elastomeric material.

18. A variable flow syringe as recited in claim 16, wherein said opening is configured such the resilient membrane maintains the opening in essentially a closed position until pressure is applied by fluid being pushed down as the plunger is advanced within the barrel, whereby the barrel can be prefilled with a fluid without substantial leakage or evaporation of the fluid during subsequent storage.

19. A variable flow syringe as recited in claim 16, wherein said resilient membrane and said opening formed therein being configured to respond to a low amount of force exerted upon said plunger such that fluid is delivered a drop at a time.

20. A variable flow syringe as recited in claim 16, wherein said resilient membrane and said opening formed therein are configured such that a high amount of force used to manually advance said barrel delivers fluid through said opening substantially in a stream.

21. A variable flow syringe as recited in claim 16, further comprising a hollow tip having a fluid dispensing end and a proximal end releasably connected to said flow discharge end of said barrel.

* * * * *

UNITED STATES PATENT AND TRADEMARK OFFICE
CERTIFICATE OF CORRECTION

PATENT NO. : 5,944,698

DATED : August 31, 1999

INVENTOR(S): Dan E. Fischer, Richard N. Rachal, Bruce S. McLean
Dan J. Bills, Doug Hyink It is certified that error appears in the above-identified patent and that said Letters Patent are hereby corrected as shown below:

Col. 1, ln. 46: before "The control" change "pense." to --pensed.--

Col. 3, ln. 19: after "a low" change "viscously" to --viscosity--

Col. 3, ln. 67: after "that these" change "drawing" to --drawings--

Col. 4, ln. 64: after "having" change "a" to --an--

Col. 5, ln. 46: after "at" and before "time" insert --a--

Col. 6, ln. 48: after "then" and before "be" insert --to--

Col. 6, ln. 62: after "fit." change "Grove" to --Groove--

Col. 7, ln. 28: before "equally" insert --are--

Col. 9, ln. 21: before "material" change "comprises" to --comprise--

Col. 9, ln. 23: after "and" change "polyvinylidene" to --polyrinylidene--

Col. 9, ln. 26: after "and" change "polyvinylidene" to --polyrinylidene--

Col. 9. ln. 66: after "flow" and before "of fluid" delete [out]

Col. 10, ln. 29: after "so as" insert --to--

UNITED STATES PATENT AND TRADEMARK OFFICE
CERTIFICATE OF CORRECTION

PATENT NO. : 5,944,698
DATED : August 31, 1999
INVENTOR(S) : Dan E. Fischer, Richard N. Rachal, Bruce S. McLean
Dan J. Bills, Doug Hyink It is certified that error appears in the above-identified patent and that said Letters Patent are hereby corrected as shown below:

Col. 10, ln. 35: after "defining" delete [,]

Col. 11, ln. 13: before "permit" insert --to--

Col. 12, ln. 43: after "such" and before "the" insert --that--

Signed and Sealed this

Twenty-seventh Day of June, 2000

Attest:

Q. TODD DICKINSON

*Attesting Officer*    *Director of Patents and Trademarks*